(12) United States Patent
Le Couedic et al.

(10) Patent No.: US 7,588,601 B2
(45) Date of Patent: Sep. 15, 2009

(54) INTERVERTEBRAL IMPLANT

(75) Inventors: Régis Le Couedic, Andresy (FR); Denis Pasquet, Quinsac (FR)

(73) Assignee: Zimmer Spine Austin, Inc., Austin, TX (US)

( * ) Notice: Subject to any disclaimer, the term of this patent is extended or adjusted under 35 U.S.C. 154(b) by 348 days.

(21) Appl. No.: 11/579,891

(22) PCT Filed: May 9, 2005

(86) PCT No.: PCT/FR2005/001140

§ 371 (c)(1),
(2), (4) Date: Nov. 9, 2006

(87) PCT Pub. No.: WO2005/120369

PCT Pub. Date: Dec. 22, 2005

(65) Prior Publication Data

US 2008/0033556 A1    Feb. 7, 2008

(30) Foreign Application Priority Data

May 11, 2004    (FR) .................................. 04 05064

(51) Int. Cl.
*A61F 2/44* (2006.01)
(52) U.S. Cl. ................. 623/17.16; 623/17.11; 606/246; 606/248; 606/249
(58) Field of Classification Search ... 623/17.11–17.16; 606/246–249
See application file for complete search history.

(56) References Cited

U.S. PATENT DOCUMENTS

D285,968 S * 9/1986 Kinnett ...................... D24/155

FOREIGN PATENT DOCUMENTS

WO    WO02071960    * 9/2002

* cited by examiner

*Primary Examiner*—Eduardo C Robert
*Assistant Examiner*—Christina Negrelli
(74) *Attorney, Agent, or Firm*—Crompton, Seager & Tufte, LLC.

(57) ABSTRACT

The invention relates to an intervertebral implant comprising a spacer constituted by first and second parts (12, 14), said parts being provided with mutual assembly means comprising first clip-fastener means (54, 56) secured to one of said parts, second clip-fastener means (49, 50) secured to the other part and suitable for co-operating with the first clip-fastener means to achieve releasable clip-fastening between the two parts, and guide means for guiding the two parts (12, 14) during clip-fastening, said guide means being distinct from the clip-fastening means and comprising:

a substantially non-deformable first guide assembly (42, 44) secured to one of said parts; and a substantially non-deformable second guide assembly (46, 48) secured to the other part to co-operate with the first guide assembly.

16 Claims, 2 Drawing Sheets

INTERVERTEBRAL IMPLANT

The present invention relates to an intervertebral implant for an ordinary portion of the spinal column, and more particularly the invention relates to the spacer of the implant.

Intervertebral spacers are devices that are well known for placing between two adjacent vertebrae in order to secure the two vertebrae to each other so as to maintain a fixed gap between them. French patent application FR 01/03362 in the name of the Applicant describes such spacers. It suffices to recall that the spacer is provided at each of its ends with a notch in which the spinous process of a vertebra is engaged. A system of ties or braids serves to secure each end of the spacer with the spinous process.

Nevertheless, putting such a spacer into place raises certain problems associated with the practice of surgery. There is a ligament known as the supraspinous ligament that interconnects the tips of all the spinous processes. In order to put the spacer into place, it is necessary to move that ligament. In practice, it is detached from the two spinous processes concerned, and it is moved away by means of a suitable surgical instrument. To detach the ligament from the spinous processes, a scalpel is used. Once the spacer has been put into place, the ligament is sewn back onto the spinous processes after making a small opening therein to receive the suture.

The major drawback of that surgical technique is that by acting on the ligament in order to detach it and then move it out of the way, it is weakened mechanically. In addition, all of those actions take time, which lengthens the duration of the surgery.

To remedy that drawback, proposals have already been made for intervertebral spacers that are made up of from two distinct portions. Each portion of the spacer is put into place on either side of the supraspinous ligament, and then by using appropriate surgical instruments, the two portions of the spacer are joined together. Such two-portion spacers are described in particular in U.S. Pat. No. 6,156,038.

Nevertheless, the two-portion spacers described in that document are relatively difficult to use. In particular, assembling the two portions of the spacer together in situ is relatively difficult and it is not certain that the two parts will together form the spacer in suitable manner.

An object of the present invention is to provide an intervertebral spacer constituted by two distinct parts that are easier for the surgeon to assemble during surgery.

To achieve this object, according to the invention, in an intervertebral implant comprising a spacer constituted by first and second parts provided with mutual assembly means, the implant is characterized in that said mutual assembly means comprise:

first clip-fastener means secured to one of said parts;

second clip-fastener means secured to the other part, suitable for co-operating with the first clip-fastener means to achieve releasable clip-fastening between the two parts in a clip-fastening direction, said first and second clip-fastening means forming integral portions of the two parts; and guide means for guiding the two parts during clip-fastening, said guide means being distinct from the clip-fastener means and comprising:

a substantially non-deformable first guide assembly secured to one of said parts; and a substantially non-deformable second guide assembly secured to the other part to co-operate with the first guide assembly so as to provide mutual guidance of the two parts along said clip-fastening direction and provide relative positioning of the two parts in a plane orthogonal to the clip-fastening direction.

It will be understood that because each part constituting the intervertebral spacer includes firstly guide means and secondly clip-fastener means, the guide means guarantee accurate relative positioning of the clip-fastener means in a manner that is easy for the surgeon. This ensures that the two parts constituting the spacer are properly assembled together, and furthermore, that this operation can be implemented more quickly than with the spacers of the prior art.

In addition, since the clip-fastener means form integral portions of the two parts, the implant is made easier for the surgeon to put into place.

In a preferred embodiment of the invention, each part of the spacer has an assembly face that is to be pressed against the assembly face of the other part when the two parts are assembled together.

Also preferably, the guide means are constituted respectively by two guide studs projecting from one of the assembly faces and by two recesses opening out into the assembly face of the other part. It is thus possible to obtain effective guidance of one of the parts relative to the other by giving the guide studs an appropriate shape.

Other characteristics and advantages of the invention appear better on reading the following description of an embodiment of the invention given by way of non-limiting example. The description refers to the accompanying figures, in which.

Figure 1:
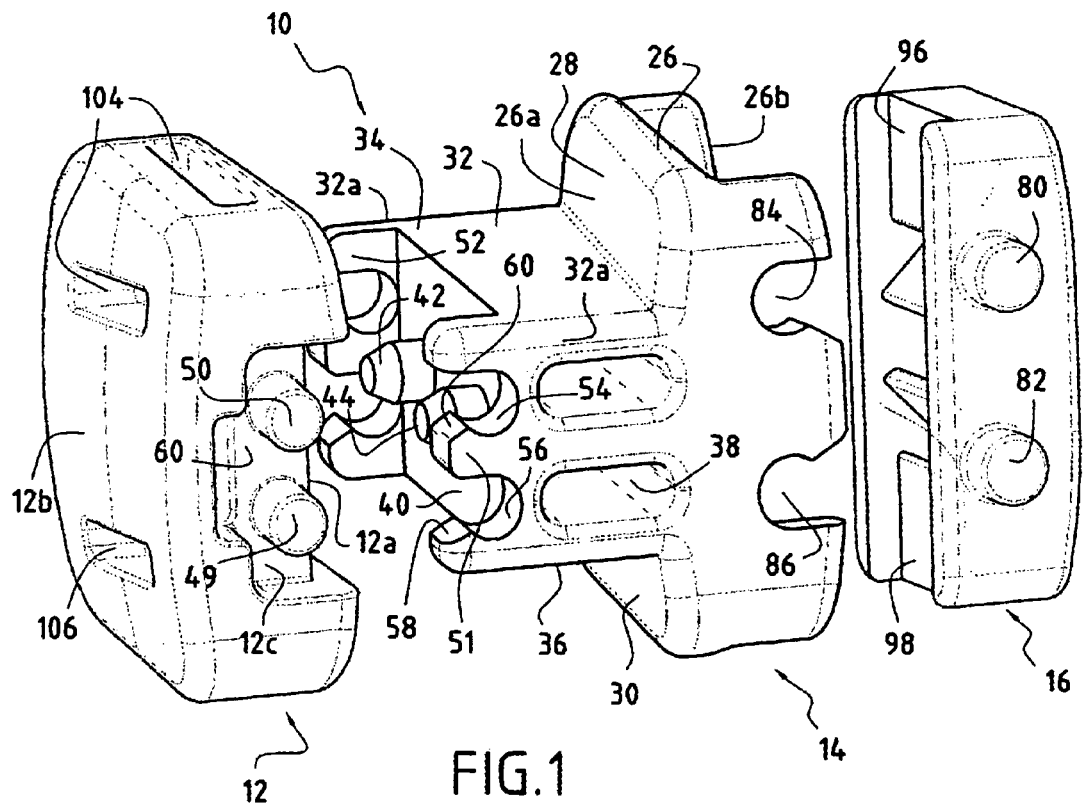
FIG. 1 is an exploded view of the various elements constituting the intervertebral implant.
Figure 2:
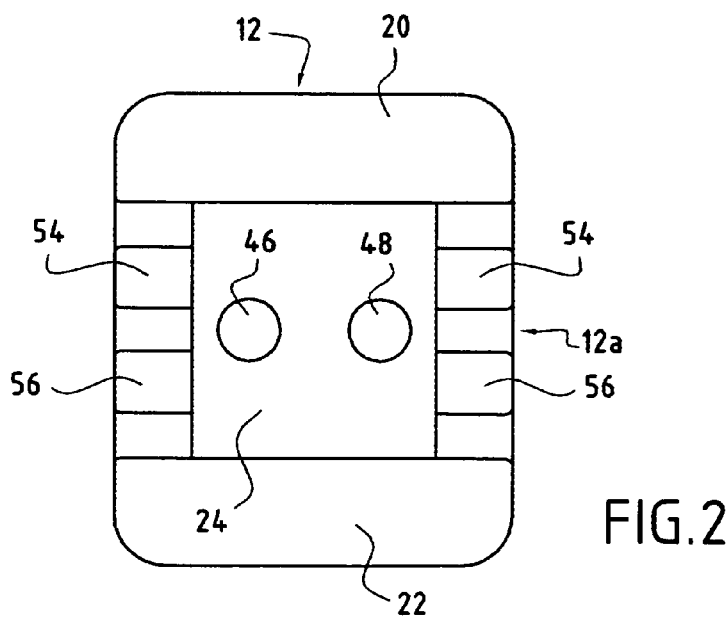
FIG. 2 is an assembly face view showing one of the two parts constituting the intervertebral spacer.

FIG. 1 shows the two parts 12 and 14 which are being assembled together serve to produce the intervertebral spacer 10. In the figure, there can also be seen a removable element 16 used for fastening purposes and for clamping braids that serve to secure two spinous processes to the spacer. The fastener element 16 is described below. The part 12 constitutes a first side piece of the intervertebral spacer. This part 12 has an inside face 12a and an outside face 12b. The inside face 12a defines a top bearing surface 20, a bottom bearing surface 22, and a middle assembly face 24.

The second part 14 also constitutes a side piece presenting an inside face 26a facing towards the inside face 12a of the part 12, and an outside face 26b. The inside face 26a of the side piece 26 defines a top bearing surface 28 and a bottom bearing surface 30. In the middle region of the inside face of the side piece 26, the part 14 has a projection 32 that projects from the central portion of the face 26a. This projection 32 or space-defining part defines two bearing surfaces, a top surface 34 and a bottom surface 36, these two faces being substantially parallel. The space-defining part 32 may include transverse recesses such as 38 for imparting a degree of resilience to this portion of the spacer. The free end of the space-defining part 32 defines an assembly face 40 for bearing against the assembly face 24 of the part 12 when the two parts constituting the spacer are assembled together.

In the assembly faces 40 and 24 of the two parts, there are provided mutual guidance means that act as these two parts move towards each other in order to secure them one to the other. Preferably, the guidance means are constituted by two guide studs 42 and 44 projecting from the assembly face 40 of the part 14 and by two blind recesses 46 and 48 formed in the assembly face 24 of the part 12. It would not go beyond the invention if only one stud were to be provided together with only one recess. Preferably, and in conventional manner, the ends of the assembly studs 42 and 44 are conical in order to provide initial positioning of the two parts. The parts 12 and 14 are secured to each other by clip-fastener means formed respectively in the side faces 12c and 12d of the part 12 and in the side faces 32a and 32b of the projection 32 of the part 14. By way of example, for the part 12 these clip-fastener means consist of two pairs of cylindrical pegs 49 and 50 and of two side walls projecting beyond the assembly face 44 of the part 14, given respective references 51 and 52. Each side wall is provided with two openings 54 and 56 suitable for receiving the pegs 49 and 50 during clip-fastening. Each opening 54, 56 includes a deformable nib 58 or 60. As also shown in FIG. 1, the pegs 49 and 50 project into a recess 60 formed in the side faces 12c, 12d of the part 12. It should naturally be added that the guide studs 42 and 44 are of a length that is longer than that of the side walls 51 and 52 defining the female clip-fastener elements. Whatever the particular implementation of the clip-fastener means, they should form integral portions respectively of the two parts 12 and 14.

Figure 3:
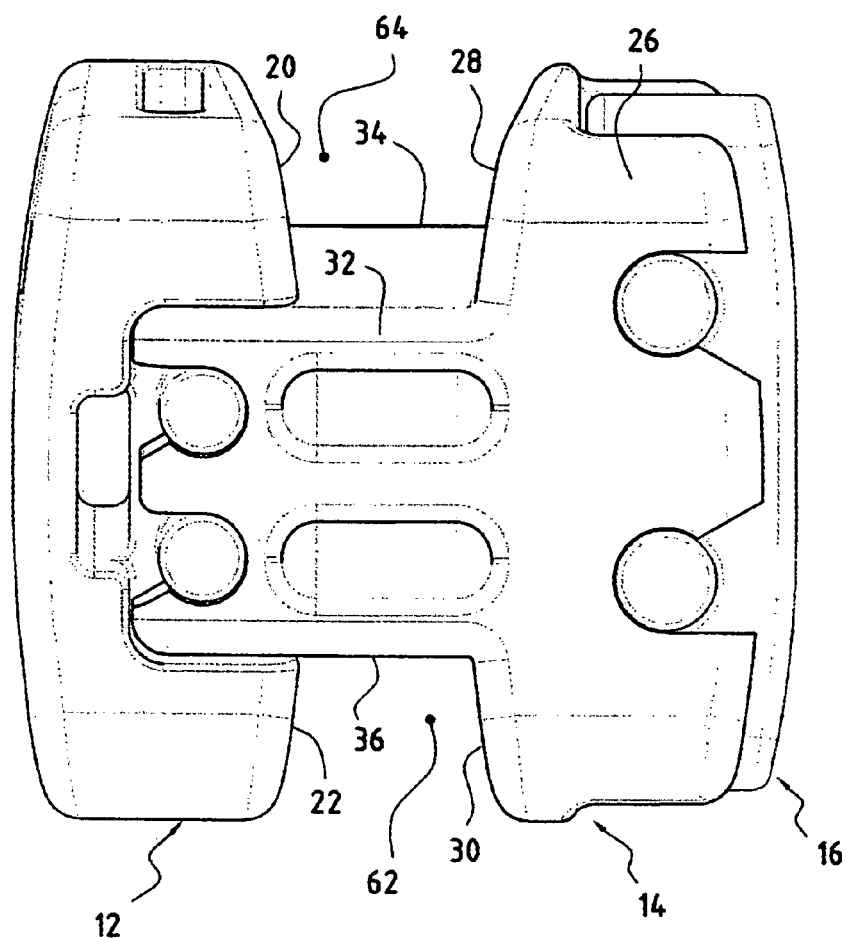
FIG. 3 is a side view of the spacer after the two parts constituting it have been assembled together.

As shown more clearly in FIG. 3, when the parts 12 and 14 are assembled together, in the manner explained below, an intervertebral spacer is obtained having the usual structure. In particular, the bearing faces 20, 22 of the part 12 and the bearing faces 28, 30 of the side piece 26 of the part 14, and finally the top and bottom faces 34 and 36 of the extension 32 define two recesses 62 and 64 for receiving the spinous processes of the two vertebrae between which the spacer is placed.

Naturally, it should be added that the guide studs 42 and 44 are of a length that is greater than that of the side walls 51 and 52 defining the female clip-fastener elements.

The above-described spacer is used as follows. The surgeon puts the spacer-constituting parts 12 and 14 into place, going round the supraspinal ligament. Using appropriate surgical instruments, the two parts are moved towards each other so as to cause the guide studs 42 and 44 to co-operate with the guide recesses 46 and 48. When the resulting relative positioning is achieved, the clip-fastener members 48, 50 and 54, 56 face one another in pairs. It then suffices for the surgeon to exert pressure on the outside faces of the two parts in order to cause the parts 12 and 14 to clip together, thus obtaining the complete spacer 10. It should be added that the clip-fastener elements 48, 50 and 54, 56 are made in such a manner as to ensure effective fastening, while still making it possible for them to be separated in the event of it being necessary to change the spacer. As explained above, it is easy to put the spacer into place since it comprises only two parts.

Figure 4:
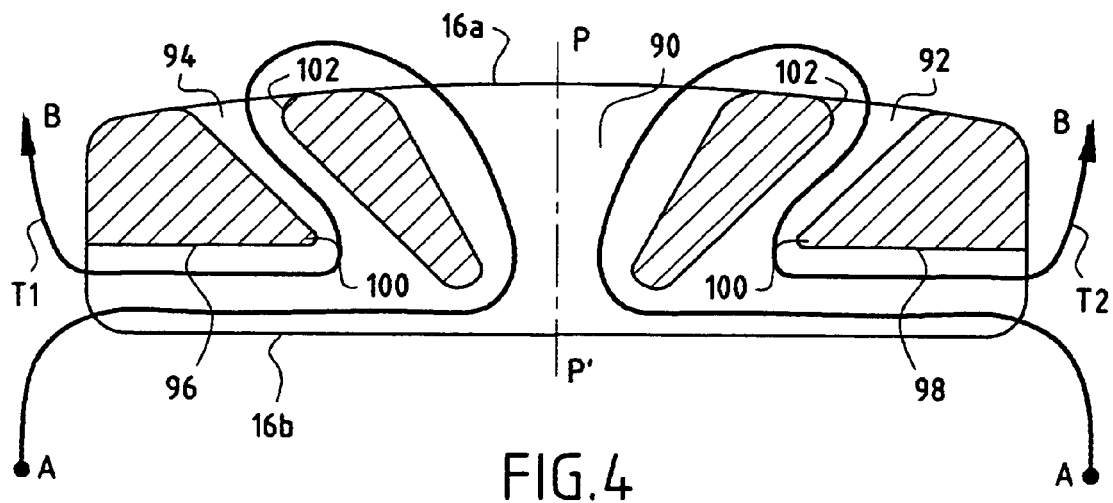
FIG. 4 is a longitudinal section of the self-locking element used for securing the braids of the implant.

With reference now to FIGS. 1 and 4, there follows a description of a preferred embodiment of the means for securing the spacer 10 to the spinous processes of the vertebrae. This system is constituted by the locking or fastener part 16 and by two braids T1 and T2. The fastener part 16 can be secured to the outside face 26b of the part 14 by clip-fastener means 80, 82, 84, and 86 that are identical to the clip-fastener means of the parts 12 and 14.

The fastener part 16 presents a clip-fastener face 16b on the part 14 and an outside face 16a. The fastener part 16 presents a plane of symmetry P, P' orthogonal to the faces 16a and 16b and parallel to the faces 32 and 34 of the extension 30 of the part 14. The locking part 16 has a central slot 90 that opens out into both faces of the part 16, and two symmetrical inclined side slots 92 and 94 that also open out into both faces of the part 16. The clip-fastener face 16b of the part 16 presents two setback surfaces 96 and 98 that extend respectively between the side slots 92 and 94 and the top and bottom ends of the part 16 which constitutes braid clamping surfaces. The slot 92 and the setback surface 98 define a first sharp edge 100. Similarly, the slot 92 and the outside face 16a of the part 16 define a second sharp edge 102 that is parallel to the edge 100. As shown in the figure, the edge 102 is further away from the midplane P, P' than is the edge 100. In addition, it should be specified that the clamping surfaces 96 and 98 are disposed in such a manner that when the part 16 is clipped onto the spacer, the distance between the face 26b of the spacer and the surface 96 or 98 is slightly less than twice the thickness of the braids T1 and T2.

Each braid T1 and T2 has a first end A that is secured to the part 12. To do this, in the example described, the part 12 is provided with a top slot 104 and a bottom slot 106 in which the ends A of the braid can form a loop. After this loop has been stitched together, the braids Ti and T2 are effectively secured to each end of the part 12. The braid T2 is engaged between the surface 98 and the face 26b of the spacer and then in the central slot 90. Thereafter, it passes over a portion of the outside face 16a of the part 16 and penetrates into the slot 62, passing over the edge 102. Thereafter, the braid T2 is engaged under the presser surface 98, between the first strand of the same braid and said surface. When the surgeon exerts traction on the end B of the braid T2, that serves to clamp the braid T2 against the spinous process of the upper or lower vertebra. The braid T1 is naturally engaged in the part 16 in the same manner in order to provide a connection with the spinous process of the other vertebra.

It will be understood that the fastener part 16 act for each of the braids as a self-locking system. When the surgeon exerts traction on the free end B of the braid, it can move without excessive friction in the slots 90 and 92 until the desired clamping effect is obtained. In contrast, when no traction is exerted on the end B of the braid, i.e. when the intervertebral implant is in normal use, a self-locking effect is obtained by the presence of the sharp edges 100 and 102 and the clamping effect of the presser surface 98 on the two strands of the braid.

In a preferred embodiment, the first clip-fastener means comprise at least two male clip-fastener members 54 and 56 that are substantially undeformable, being disposed on either side of the assembly surface 24, and second clip-fastener means comprising at least two clip-fastener female members 49 and 50 that are elastically deformable and disposed on either side of the assembly surface 40.

Also preferably, said first guide assembly comprises at least one guide stud 42 and 44 projecting from an assembly face 40 of one of the parts and at least one recess 46 and 48 opening out into the assembly face 24 of the other part.

The invention claimed is:

1. An intervertebral implant comprising a spacer including first and second parts, said first and second parts being provided with mutual assembly means, said mutual assembly means comprising:

first clip-fastener means secured to one of said first and second parts;

second clip-fastener means secured to the other of the first and second parts for co-operating with the first clip-fastener means to achieve releasable clip-fastening between the first and second parts in a clip-fastening direction, said first and second clip-fastening means forming integral portions of the first and second parts; and guide means for guiding the first and second parts during clip-fastening, said guide means being distinct from the first and second clip-fastener means and comprising:

a substantially non-deformable first guide assembly located on an assembly face of one of said first and second parts; and a substantially non-deformable second guide assembly located on an assembly face of the other of the first and second parts to co-operate with the first guide assembly so as to provide mutual guidance of the first and second parts along said clip-fastening direction and provide relative positioning of the first and second parts in a plane orthogonal to the clip-fastening direction;

wherein each of said first and second parts has an assembly face, said assembly faces being pressed one against the other when the first and second parts are assembled together along an assembly interface; and wherein said first guide assembly comprises at least one guide stud projecting from the assembly face of one of the first and second parts, and the second guide assembly comprises at least one recess opening out into the assembly face of the other of the first and second parts.

2. An intervertebral implant according to claim 1, wherein the first clip-fastener means comprise at least two substantially non-deformable male clip-fastener members disposed on either side of the assembly interface, and the second clip-fastener means comprise at least two elastically deformable female clip-fastener members disposed on either side of the assembly interface.

3. An intervertebral implant according to claim 1, wherein said first guide assembly comprises two guide studs and the second guide assembly comprises two recesses.

4. An intervertebral implant according to claim 1, wherein each of said first and second parts includes two clip-fastener means.

5. An implant according to claim 1, wherein the first part has an outside face opposite to the assembly face, of the first part, and wherein the spacer further comprises:
    two braids for fastening said spacer on two spinous processes; and
    a self-locking element comprising fastener means detachably coupling the self-locking element to the second part opposite the outside face of the first part;
    each braid having a first end secured to said first part and a second end that is engageable in said self-locking element.

6. An intervertebral implant according to claim 1, further comprising a fastener element detachably coupled to the second part.

7. An intervertebral implant according to claim 6, further comprising:
    a first band for securing the spacer to a first spinous process, the first band attached to the first part and passing through a first slot extending though the fastener element; and
    a second band for securing the spacer to a second spinous process, the second band attached to the first part and passing though a second slot extending though the fastener element.

8. An intervertebral implant according to claim 7, wherein a portion of the first band is positioned along an interface between the second part and the fastener element, and a portion of the second band is positioned along the interface between the second part and the fastener element.

9. An intervertebral implant according to claim 8, wherein the portion of first band is pressed between the second part and the fastener element when the second part is detachably coupled to the fastener element, and the portion of the second band is pressed between the second part and the fastener element when the second part is detachably coupled to the fastener element.

10. An intervertebral implant according to claim 1, wherein the at least one stud is conical.

11. The intervertebral implant according to claim 1, wherein during assembly of the first part to the second part, the at least one stud engages the at least one recess before the first clip-fastener means engages the second clip-fastener means.

12. An intervertebral implant according to claim 1, wherein the first part is detachably coupled to the second part on a first side of the second part, and wherein the spacer further comprises:
    a fastener part detachably coupled to the second part on a second side of the second part opposite the first side; and
    two bands for fastening said spacer on two spinous processes; and
    wherein each band has a first end secured to said first part and a second end that passes through a slot of the fastener part.

13. An intervertebral implant comprising:
    a spacer including a first part, a second part, and a third part, wherein the first part is detachably coupled to a first side of the second part, and the third part is detachably coupled to a second side of the second part opposite the first part;
    wherein the first part is provided with a first clip-fastener means, the second part is provided with a second clip-fastener means and a third clip-fastener means, and the third part is provided with a fourth clip-fastener means;
    wherein the first clip-fastener means co-operates with the second clip-fastener means to achieve releasable clip-fastening between the first and second parts in a first clip-fastening direction;
    wherein the third clip-fastener means co-operates with the fourth clip-fastener means to achieve releasable clip-fastening between the second and third parts in a second clip-fastening direction;
    a first band for securing the spacer to a first spinous process, the first band attached to the first part and passing through a first slot extending through the third part; and
    a second band for securing the spacer to a second spinous process, the second band attached to the first part and passing through a second slot extending through the third part.

14. An intervertebral implant according to claim 13, further comprising:
    guide means for guiding the first and second parts during clip-fastening, said guide means being distinct from the first and second clip-fastener means and comprising:
        a substantially non-deformable first guide assembly secured to one of said first and second parts; and
        a substantially non-deformable second guide assembly secured to the other of the first and second parts to co-operate with the first guide assembly so as to provide mutual guidance of the first and second parts along said first clip-fastening direction and provide relative positioning of the first and second parts in a plane orthogonal to the first clip-fastening direction.

15. An intervertebral implant according to claim 14, wherein a portion of the first band is positioned along an interface between the second part and the third part, and a portion of the second band is positioned along the interface between the second part and the third part.

16. An intervertebral implant according to claim 15, wherein the portion of first band is pressed between the second part and the third part when the second part is detachably coupled to the third part, and the portion of the second band is pressed between the second part and the third part when the second part is detachably coupled to the third part.

* * * * *

UNITED STATES PATENT AND TRADEMARK OFFICE
CERTIFICATE OF CORRECTION

PATENT NO. : 7,588,601 B2 Page 1 of 1
APPLICATION NO. : 11/579891
DATED : September 15, 2009
INVENTOR(S) : Regis Le Couedic et al.

It is certified that error appears in the above-identified patent and that said Letters Patent is hereby corrected as shown below:

Column 5
Line 41, delete "though", and insert therefor -- through --.
Line 45, delete "though", and insert therefor -- through --.

Signed and Sealed this

Thirtieth Day of March, 2010

David J. Kappos
*Director of the United States Patent and Trademark Office*